United States Patent
Conte

(10) Patent No.: US 11,389,424 B2
(45) Date of Patent: Jul. 19, 2022

(54) METHODS AND COMPOSITIONS FOR TREATING CHEMOTHERAPY-INDUCED DIARRHEA

(71) Applicant: NAPO PHARMACEUTICALS, INC., San Francisco, CA (US)

(72) Inventor: Lisa A. Conte, San Francisco, CA (US)

(73) Assignee: NAPO PHARMACEUTICALS, INC., San Francisco, CA (US)

( * ) Notice: Subject to any disclaimer, the term of this patent is extended or adjusted under 35 U.S.C. 154(b) by 0 days.

(21) Appl. No.: 15/917,357

(22) Filed: Mar. 9, 2018

(65) Prior Publication Data

US 2020/0345687 A1    Nov. 5, 2020

Related U.S. Application Data

(60) Provisional application No. 62/469,133, filed on Mar. 9, 2017.

(51) Int. Cl.

| | |
|---|---|
| A61K 31/353 | (2006.01) |
| A61K 36/47 | (2006.01) |
| A61P 1/12 | (2006.01) |
| A61K 9/48 | (2006.01) |
| A61K 9/28 | (2006.01) |
| A61K 45/06 | (2006.01) |

(52) U.S. Cl.
CPC .............. *A61K 31/353* (2013.01); *A61K 9/28* (2013.01); *A61K 9/4891* (2013.01); *A61K 36/47* (2013.01); *A61K 45/06* (2013.01); *A61P 1/12* (2018.01)

(58) Field of Classification Search
None
See application file for complete search history.

(56) References Cited

U.S. PATENT DOCUMENTS

| 8,962,680 B2 | 2/2015 | Forbes |
| 2012/0202876 A1 | 8/2012 | Verkman |
| 2016/0067311 A1 | 3/2016 | Giorgino |

FOREIGN PATENT DOCUMENTS

| WO | 2016112312 A1 | 7/2016 |
| WO | 2018106845 A1 | 6/2018 |

OTHER PUBLICATIONS

Gao et al., "HALT-D: A Phase II Evaluation of Crofelemer for the Prevention and Prophylaxis of Diarrhea in Patients With Breast Cancer on Pertuzumab-Based Regimens", Clinical Breast Cancer, Aug. 27, 2016, vol. 17(1), pp. 76-78.*
Abbas et al., "A double-blind, randomized, multiple-dose, parallel-group study to characterize the occurrence of diarrhea following two different dosing regimens of neratinib, an irreversible pan-ErbB receptor tyrosine kinase inhibitor", Cancer Chemotherapy and Pharmacology, 2012, vol. 70, pp. 191-199.*
Salix Pharmaceuticals, "FULYZAQ Full Prescribing Information", Dec. 2012, downloaded from "https://www.accessdata.fda.gov/drugsatfda_docs/label/2012/202292s000lbl.pdf", 11 pages.*
Van Sebille et al., "ErbB small molecule tyrosine kinase inhibitor (TKI) induced diarrhoea: Chloride secretion as a mechanistic hypothesis", Cancer Treatment Reviews, vol. 41 (2015), pp. 646-652.*
Rugo et al "The characterization, management, and future considerations for ErbB-family TKI-associated diarrhea", Breast Cancer Research and Treatment, 2019, vol. 175, p. 5-15 [Published online: Jan. 22, 2019]; https://doi.org/10.1007/st10549-018-05102-x. Entire Document.
International Search Report, PCT/US 20/38691, dated Nov. 23, 2020, Karsten Manuf. Corp.
Van Sebille YZ, Gibson RJ, Wardill HR, et al. ErbB small molecule tyrosine kinase inhibitor (TKI) induced diarrhoea: Chloride secretion as a mechanistic hypothesis. Cancer Treat Rev 2015; 41: 646-52.
Bowen JM et al. Development of a rat model of oral small molecule receptor tyrosine kinase inhibitor-induced diarrhea. Cancer Biol Ther 2012; 13(13):1269-75.
Bowen JM. Mechanisms of TKI-induced diarrhea in cancer patients. Curr Opin Support Palliat Care 2013;7(2):162-7.
Bowen JM et al. Determining the mechanisms of lapatinib-induced diarrhoea using a rat model. Cancer Chemother Pharmacol 2014;74(3):617-27.
Yang et al, Expert Rev. Anticancer Ther. 13(6), 729-736 (2013), "Diarrhea associated with afatinib: an oral ErbB family blocker".
Hirsh, V., Blais, N., Burkes, R., Verma, S., & Croitoru, K. (2014). Management of diarrhea induced by epidermal growth factor receptor tyrosine kinase inhibitors. Current Oncology, 21(6), 329-336. https://doi.org/10.3747/co.21.2241.
Van Sebille et al, Curr Opin Support Palliat Care, 2016, vol. 10(2) 152-156.
Chan et al, Ther Adv Med Oncol, 2016, vol. 8(5) 339-350.
Al-Dasooqi, Noor et al., "HER2 Targeted Therapies for Cancer and the Gastrointestinal Tract", Current Drug Targets, 2009, vol. 10, pp. 537-542.
Al-Dasooqi, Noor et al., "Matrix metalloproteinases: key regulators in the pathogenesis of chemotherapy-induced mucositis?", Cancer Chemother Pharmacol, 2009, vol. 64, pates 1-6.
Van Sebille, Y et al., "Dacomitinib-induced diarrhea: targeting chloride secretion with crofelemer", Accepted Article, doi: 10.1002/ilc.31048, International Journal of Cancer, 2017, pp. 1-31.
Van Sebille Y et al., "Dacomitinib-induced diarrhea is associated with altered gastroinstestinal permeability and disruption in ileal histology in rats", Int. J. Cancer: 140, 2820-2829. (2017).

* cited by examiner

*Primary Examiner* — Savitha M Rao
*Assistant Examiner* — Gregg Polansky
(74) *Attorney, Agent, or Firm* — Ballard Spahr, LLP

(57) ABSTRACT

Presented herein are methods for treating diarrhea by administering to a patient in need thereof, an inhibitor of chloride-ion transport in an amount sufficient to treat diarrhea. Treatment of diarrhea includes the treatment of the diarrhea as well as the pain, abdominal discomfort and other symptoms associated with diarrhea. In one embodiment, the inhibitor of chloride-ion transport is crofelemer.

16 Claims, No Drawings

METHODS AND COMPOSITIONS FOR TREATING CHEMOTHERAPY-INDUCED DIARRHEA

CROSS REFERENCE TO RELATED APPLICATION

This application claims priority to U.S. Provisional Application No. 62/469,133, filed Mar. 9, 2017. The contents of which are incorporated by reference in their entirety.

FIELD OF THE INVENTION

The present invention is directed to methods of preventing, ameliorating and/or treating diarrhea. More specifically, the methods presented herein prevent, ameliorate or treat chemotherapy-induced diarrhea (CID) using a proanthocyanidin such as crofelemer in combination with a chemotherapy agent.

BACKGROUND

Diarrhea is a common occurrence in human cancer patients that can result from radiotherapy, chemotherapeutic agents, decreased physical performance, graft versus host disease and infections or a combination thereof. In particular, chemotherapy-induced diarrhea (CID) is common, especially in patients with advanced cancer, and has to be assessed for etiologies associated with the chemotherapeutic regimen or not [Gibson, R. and Stringer, A., Curr Opin Support Palliat Care 3: 31-35, 2009]. Careful analysis can result in better management of the diarrheal symptoms to prevent severe complications that may be irreversible [Davila, M. and Bresalier, R., Nat Clin Pract Gastroenterol Hepatol 5: 682-696, 2008; Vincenzi, B. et al. Nat Clin Pract Oncol 5: 455-465, 2008]. Sequelae can include dehydration, malnutrition, cardiovascular issues, and even death.

CID is very prevalent depending on the chemotherapy regime with an estimated prevalence of between about 50-80% in patients [Benson, A. et al. J Clin Oncol 22: 2918-2926, 2004; Gibson, R. and Stringer, A., Curr Opin Support Palliat Care 3: 31-35, 2009] especially those treated with 5-fluorouracil bolus or some combination therapies of irinotecan and fluoropyrimidines (IFL, XELIRI). Regardless of the molecular targeted approach of tyrosine kinase inhibitors and antibodies, diarrhea is a common side effect in up to 60% of patients with up to 10% having severe diarrhea. Furthermore, the underlying pathophysiology is still under investigation.

Therapeutic agents commonly causing diarrhea include 5-fluorouracil (5-FU), capecitabine and irinotecan (CPT-11) [Benson, A. et al. J Clin Oncol 22: 2918-2926, 2004; Keefe, D. et al. Semin Oncol Nurs 20: 38-47, 2004]. It is often a dose-related adverse effect and may be associated with other features of toxicity. CID appears to be a multifactorial process whereby acute damage to the intestinal mucosa (including loss of intestinal epithelium, superficial necrosis and inflammation of the bowel wall) causes an imbalance between absorption and secretion in the small bowel [Keefe, D. et al. Gut 47: 632-637, 2000; Keefe, D. Support Care Cancer 15: 483-490, 2007; Gibson, R. and Stringer, A., Curr Opin Support Palliat Care 3: 31-35, 2009].

Left untreated, life-threatening gastrointestinal syndrome is recognized by two National Cancer Institute-sponsored cooperative group trials as a serious complication. These trials reviewed early toxic deaths occurring in irinotecan plus high-dose fluorouracil and leucovorin for advanced colorectal cancer and highlighted the need for vigilant monitoring and aggressive therapy for this serious complication [Conti, J. et al. J Clin Oncol 14: 709-715, 1996; Arbuckle, R. et al. Oncologist 5: 250-259, 2000; Saltz L. et al. N Engl J Med 343: 905-914, 2000]. In addition, diarrhea can hinder chemotherapy and other treatments for cancer by causing dosing delays, reductions, or use of alternative agents which may have an ultimate impact on survival [Engelking, C. et al., Oncol Nurs Forum 25: 859-860 1998; Ippoliti, A., Am J Health Syst Pharm 55: 1573-1580, 1998].

Therefore, drug-related diarrhea in human subjects undergoing chemotherapy represents an important and unmet clinical need requiring more effective management. Currently prescribed therapies are only partially effective or are plagued by unacceptable side effects such as constipation and the potential for addiction. The development of a drug for the treatment of chemotherapy-associated diarrhea with a low potential for drug-drug interactions, effects on drug metabolism, or abuse potential would provide an important benefit for subjects undergoing chemotherapy.

SUMMARY

Disclosed herein are methods of preventing, ameliorating and/or treating diarrhea in human subjects being administered or having been administered a chemotherapy regimen. In one embodiment, the methods presented herein prevent, ameliorate or treat chemotherapy-induced diarrhea (CID).

In one aspect, provided herein are methods of treating CID in a human subject undergoing chemotherapy, particularly for cancer treatment, comprising administering to a subject in need thereof a composition comprising an effective amount of a proanthocyanidin polymer composition from *C. lechleri*, preferably crofelemer, to treat, ameliorate or prevent CID. In certain embodiments, the crofelemer is an enterically protected formulation. In certain embodiments the chemotherapy is administered to treat, ameliorate, manage or prevent cancer.

According to certain embodiments, crofelemer may be administered in combination with other chemotherapy agents.

In one embodiment, the crofelemer is administered at the same time as administration of chemotherapy to reduce or delay the onset of CID.

In certain embodiments, the subject exhibits Grade 1, Grade 2, Grade 3 or Grade 4 diarrhea in accordance with the Common Toxicity Criteria from the National Cancer Institute.

In one embodiment, the crofelemer is administered before administration of chemotherapy to reduce or delay the onset of CID.

In one embodiment, the crofelemer is administered after administration of chemotherapy to reduce the onset of or treat CID.

In certain embodiments, the crofelemer is administered to reduce the risk, incidence or severity of CID so that the human subject can tolerate a particular chemotherapy agent with CID as a side effect or a higher dose of a chemotherapy agent that has CID as a side effect.

In one embodiment, the chemotherapy agent is selected from alkylating agents, anthracyclines, cytoskeletal disruptors (taxanes), epothilones, histone deacetylase inhibitors, inhibitors of topoisomerase I, inhibitors of topoisomerase II, kinase inhibitors, nucleotide analogs and precursor analogs, peptide antibiotics, platinum-based agents and retinoids In one embodiment, the chemotherapy agent comprises one or more tyrosine kinase inhibitors.

In one embodiment, the tyrosine kinase inhibitor is selected from lapatinib, sunitinib, sorafenib, erlotinib, gefitinib, axitinib, imatinib, nilotinib, dasatinib, cabozantinib, ruxolitinib, neratinib, bosutinib and valatinib.

In one embodiment, the chemotherapy comprises one or more HER of hEGFR (Human epidermal growth factor receptor) inhibitors.

In one embodiment, the HER inhibitor is selected from RG7116, RG1273 (pertuzumab, Perjeta®), RG3502 (trastuzumab emantasine, T-DMI), RG597 (trastuzumab, HERCEPTIN), RGA201 (RG7160), erlotinib (Tarceva®), dacomitinib (PF-00299804), PF-05280014 (Pfizer's biosimilar mAB to RG597).

In various embodiments, the chemotherapy regiment comprises two or more HER inhibitors, such as trastuzumab and pertuzumab, and one or more chemotherapy agents, such as, a taxane like docetaxel or paclitaxel. In various embodiments, the chemotherapy regiment further comprises a platinum-based antineoplastic such as carboplatin.

In various embodiments, the chemotherapy regiment comprises a HER inhibitors, such as trastuzumab or pertuzumab, a tyrosine kinase inhibitor, such as neratinib, and a taxane, such as, docetaxel or paclitaxel. In various embodiments, the chemotherapy regiment further comprises a platinum-based antineoplastic such as carboplatin.

In various embodiments, the chemotherapy regiment is administered once every three weeks.

In various embodiments, the crofelemer is administered after a subject begins to exhibit symptoms of CID.

In certain embodiments, the crofelemer is administered for the duration of treatment with the chemotherapy.

In certain embodiments, the subject is undergoing chemotherapy to treat one or more forms of cancer, such as breast cancer.

In certain embodiments, the crofelemer is administered until symptoms of CID are ameliorated and then crofelemer is discontinued.

In various embodiments, the administration comprises: administering about 250 mg to about 1000 mg per day; administering about 250 mg per day; administering about 500 mg per day; administering about 1000 mg per day; administering about 125 mg two times per day; administering about 250 mg two times per day; or administering about 500 mg two times per day of crofelemer, particularly, enterically protected crofelemer formulated as a tablet for oral administration, to a subject in need thereof. In other embodiments, the crofelemer is formulated for oral administration but is not enterically protected, e.g., does not have an enteric coating. In other embodiments, the dosage of the proanthocyanidin polymer composition is bioequivalent to about 250 mg to about 1000 mg per day; about 250 mg per day; about 500 mg per day; about 1000 mg per day; about 125 mg two times per day; about 250 mg two times per day; or about 500 mg two times per day of an oral dosage form of crofelemer that enterically protected.

In one aspect, presented herein are methods of treating stool consistency in a subject undergoing chemotherapy, comprising: administering about 250 mg to about 1000 mg per day; administering about 250 mg per day; administering about 500 mg per day; administering about 1000 mg per day; administering about 125 mg two times per day; administering about 250 mg two times per day; or administering about 500 mg two times per day of crofelemer, particularly, enterically protected crofelemer formulated as a tablet for oral administration, to a subject in need thereof (or is a dosage of a proanthocyanidin polymer composition that is bioequivalent to the dosage of an enteric protected formulation of crofelemer).

In one aspect, presented herein are methods of improving stool consistency in a subject undergoing chemotherapy, comprising: administering about 250 mg to about 1000 mg per day; administering about 250 mg per day; administering about 500 mg per day; administering about 1000 mg per day; administering about 125 mg two times per day; administering about 250 mg two times per day; or administering about 500 mg two times per day of crofelemer, particularly, enterically protected crofelemer formulated as a tablet for oral administration, to a subject in need thereof (or is a dosage of a proanthocyanidin polymer composition that is bioequivalent to the dosage of an enteric protected formulation of crofelemer).

In one aspect, presented herein are methods of alleviating watery diarrhea in a subject undergoing chemotherapy, comprising: administering about 250 mg to about 1000 mg per day; administering about 250 mg per day; administering about 500 mg per day; administering about 1000 mg per day; administering about 125 mg two times per day; administering about 250 mg two times per day; or administering about 500 mg two times per day of crofelemer, particularly, enterically protected crofelemer formulated as a tablet for oral administration, to a subject in need thereof (or is a dosage of a proanthocyanidin polymer composition that is bioequivalent to the dosage of an enteric protected formulation of crofelemer).

In one aspect, presented herein are methods of decreasing the number of bowel movements per day in a subject undergoing chemotherapy, comprising: administering about 250 mg to about 1000 mg per day; administering about 250 mg per day; administering about 500 mg per day; administering about 1000 mg per day; administering about 125 mg two times per day; administering about 250 mg two times per day; or administering about 500 mg two times per day of crofelemer, particularly, enterically protected crofelemer formulated as a tablet for oral administration, to a subject in need thereof (or is a dosage of a proanthocyanidin polymer composition that is bioequivalent to the dosage of an enteric protected formulation of crofelemer).

The dosages may be the amount of a composition containing a proanthocyanidin polymer composition from *C. lechleri* that is bioequivalent to the dose of an enteric protected formulation of crofelemer.

In one embodiment, a human subject is considered treated if the subject demonstrates one or more of a decrease in the number of bowel movements per day, a decrease in the number of watery bowel movements per day, an improvement in the daily or weekly abdominal score for pain or discomfort, an improvement in the score for daily stool consistency, a decrease in stool consistency score (from watery to formed), a decrease in the number of days per week that subjects experienced urgency, a decrease in the number of days per week that the subject experienced fecal incontinence.

In one embodiment, a human subject is considered treated if the subject demonstrates an improvement in the score for daily stool consistency.

In one embodiment, a human subject is considered treated if the subject demonstrates a decrease in stool consistency.

In one embodiment, a human subject is considered treated if the subject demonstrates a decrease in the number of watery bowel movements per day.

In one embodiment, a human subject is considered treated if the subject demonstrates a decrease in the number of bowel movements per day.

In one embodiment, symptoms increased or decreased are measured from a baseline.

In one embodiment, the administering is for the duration of the chemotherapy.

In one embodiment, the administering occurs for about 1 to about 6 weeks longer than the chemotherapy cycle.

In one embodiment, the administering occurs for about 3 to 12 weeks.

Other embodiments are disclosed below.

DETAILED DESCRIPTION

Certain chemotherapies may cause chemotherapy-induced diarrhea (CID) is a human subject that may cause distress, adversely impact the subject's health and wellbeing, make the chemotherapy difficult to tolerate such that the subject has to take a lower dose or go off of the chemotherapeutic agent or switch to a different treatment regimen that may be, but for the CID, more effective for the treatment of cancer. Proanthocyanidin polymer compositions of *C. lechleri*, particularly, crofelemer, and more particularly, enteric coated crofelemer formulated for oral administration, but also SB300, reduce, ameliorate, prevent or eliminate the CID symptoms in a subject undergoing chemotherapy. Thus, administration of crofelemer, or other proanthocyanidin polymer composition of *C. lechleri* may permit subjects to tolerate either certain chemotherapeutic regimens, or to tolerate higher, more effective, doses of certain chemotherapeutic regimens.

The methods disclosed herein involved the administration of effective amounts of a proanthocyanidin polymer, e.g., crofelemer, to subjects undergoing chemotherapy having, for example, chemotherapy-induced diarrhea (CID) or at risk of developing CID.

I. Definitions

Where a term is provided in the singular, the inventors also contemplate aspects of the invention described by the plural of that term. As used in this specification and in the appended claims, the singular forms "a", "an" and "the" include plural references unless the context clearly dictates otherwise, e.g., "a compound" includes a plurality of compounds. Thus, for example, a reference to "a method" includes one or more methods, and/or steps of the type described herein and/or which will become apparent to those persons skilled in the art upon reading this disclosure.

"Ameliorate," "amelioration," "improvement" or the like refers to, for example, a detectable improvement or a detectable change consistent with improvement that occurs in a subject or in at least a minority of subjects, e.g., in at least about 2%, 5%, 10%, 15%, 20%, 25%, 30%, 40%, 50%, 60%, 70%, 75%, 80%, 85%, 90%, 95%, 98%, 100% or in a range between about any two of these values. Such improvement or change may be observed in treated subjects as compared to subjects not treated with crofelemer, where the untreated subjects have, or are subject to developing, the same or similar disease, condition, symptom or the like. Amelioration of a disease, condition, symptom or assay parameter may be determined subjectively or objectively, e.g., self-assessment by a subject(s), by a clinician's assessment or by conducting an appropriate assay or measurement. Amelioration may be transient, prolonged or permanent or it may be variable at relevant times during or after crofelemer is administered to a subject or is used in an assay or other method described herein or a cited reference, e.g., within timeframes described infra, or about 1 hour after the administration or use of crofelemer to about 7 days, 2 weeks, 28 days, or 1, 3, 6, 9 months or more after a subject(s) has received such treatment.

The "modulation" of, e.g., a symptom, level or biological activity of a molecule, or the like, refers, for example, that the symptom or activity, or the like is detectably increased or decreased. Such increase or decrease may be observed in treated subjects as compared to subjects not treated with crofelemer, where the untreated subjects have, or are subject to developing, the same or similar disease, condition, symptom or the like. Such increases or decreases may be at least about 2%, 5%, 10%, 15%, 20%, 25%, 30%, 40%, 50%, 60%, 70%, 75%, 80%, 85%, 90%, 95%, 98%, 100%, 150%, 200%, 250%, 300%, 400%, 500%, 1000% or more or within any range between any two of these values. Modulation may be determined subjectively or objectively. Modulation may be transient, prolonged or permanent or it may be variable at relevant times during or after crofelemer is administered to a subject or is used in an assay or other method described herein or a cited reference, e.g., within times descried infra, or about 1 hour of the administration or use of crofelemer to about 2 weeks, 28 days, 3, 6, 9 months or more after a subject(s) has received crofelemer.

As used herein, "subject" includes an animal, including a human, undergoing chemotherapy and having or being at risk for CID or who could otherwise benefit from the administration of crofelemer as described herein, such as a human subject.

The language "a therapeutically effective amount" of a compound refers to an amount of crofelemer which is effective, upon single or multiple dose administration to the subject, in treating, managing, or ameliorating the symptoms of the chemotherapy induced diarrhea.

The language "a prophylactically effective amount" of a compound refers to an amount of crofelemer which is effective, upon single or multiple dose administration to the subject, in preventing CID.

The term "administration" or "administering" includes routes of introducing crofelemer to a subject to perform its intended function. Examples of routes of administration that may be used include injection, oral, inhalation, vaginal, rectal and transdermal. The pharmaceutical preparations may be given by forms suitable for each administration route. For example, these preparations are administered in tablet or capsule form, by injection, inhalation, ointment, or suppository. Administration may also be by injection, infusion or inhalation; topical by lotion or ointment; and rectal by suppositories. Oral administration is preferred. Depending on the route of administration, crofelemer can be coated with or disposed in a selected material to protect it from natural conditions that may detrimentally affect its ability to perform its intended function. Crofelemer can be administered alone, or in conjunction with either another agent or agents as described above or with a pharmaceutically-acceptable carrier, or both. Exemplary enteric coated forms of crofelemer are described in, for example, U.S. Pat. No. 7,556,831.

Administration "in combination with" one or more further therapeutic agents includes simultaneous (concurrent) and consecutive administration in any order.

The phrase "pharmaceutically acceptable" refers to crofelemer as described herein, compositions containing crofelemer, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" includes pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body.

The term "treat" or "treatment" as used herein is intended to include the reduction or amelioration of the progression, severity, and/or duration of a condition or one or more symptoms caused by chemotherapy or resulting from the administration of one or more therapies.

For example, treating CID may include an improvement of the following symptoms of CID, including, for example, a decrease in the number of bowel movements per day (frequency), a decrease in the number of watery bowel movements per day, a decrease in symptom frequency (urgency, fecal incontinence), a decrease in symptom severity (abdominal pain or discomfort), a decrease in daily stool consistency score (watery to formed), or a decrease in stool consistency leading to formed stools from watery stools. The severity of chemotherapy induced diarrhea may be characterized according to Common Toxicity Criteria for diarrhea, adapted from the National Cancer Institute (see, e.g., Stein et al., *Ther. Adv. Med. Oncol.* 2:51-43 (2010). In this criteria, Grade 1 is an increase of greater than 4 stools per day over baseline (or mild increase in ostomy output compared to baseline); Grade 2 is an increase of 4 to 6 stools per day over baseline (moderate increase in ostomy output compared to baseline); Grade 3 is an increase in greater than 7 stools per day over baseline, with incidences of incontinence and hospitalization indicated (severe increase in ostomy output compared to baseline); and Grade 4 is life-threatening consequences with urgent intervention indicated. Thus, treatment may include reduction in one, two or three grades of the criteria.

The term "obtaining" as in "obtaining crofelemer" is intended to include purchasing, synthesizing, isolating, extracting or otherwise acquiring crofelemer.

The term "tolerate" or "tolerance" as in tolerating a particular chemotherapeutic agent means that the subject does not suffer side effects so severe that they compromise the health and wellbeing of the subject to such an extent that the detriment outweighs the benefit of the chemotherapy or the subject is non-compliant with the chemotherapeutic regimen due to the side effects.

II. Active Compounds

A. Proanthocyanidins

Proanthocyanidins are a group of condensed tannins. Crude extracts from medicinal plants, for example, *Pycanthus angolenis* and *Baphia nitida*, have been shown to have antidiarrheal qualities in animal tests (Onwukaeme and Anuforo, 1993, Discovery and Innovation, 5:317; Onwukaeme and Lot, 1991, Phytotherapy Res., 5:254). Crude extracts which contain tannins, in particular extracts from carob pods and sweet chestnut wood, have been proposed as treatments or prophylactics (U.S. Pat. No. 5,043,160; European Patent No. 481,396).

Proanthocyanidins are comprised of at least two or more monomer units that may be of the same or different monomeric structure. The monomer units (generally termed "leucoanthocyanidin") are generally monomeric flavonoids which include catechins, epicatechins, gallocatechins, galloepicatechins, flavanols, flavonols, and flavan-3,4-diols, leucocyanidins and anthocyanidins. Therefore, the polymer chains are based on different structural units, which create a wide variation of polymeric proanthocyanidins and a large number of possible isomers (Hemingway et al., 1982, J. C. S. Perkin, 1:1217). Larger polymers of the flavonoid 3-ol units are predominant in most plants, and are found with average molecular weights above 2,000 daltons, containing 6 or more units (Newman et al., 1987, Mag. Res. Chem., 25:118).

Proanthocyanidin polymers are found in a wide variety of plants, particularly those with a woody habit of growth (e.g., *Croton* spp. and *Calophyllum* spp.). A number of different *Croton* tree species, including *Croton sakutaris*, *Croton gossypifolius*, *Croton palanostima*, *Croton lechleri*, *Croton erythrochilus* and *Croton draconoides*, found in South America, produce a red viscous latex sap called Sangre de Drago or "Dragon's Blood". U.S. Pat. No. 5,211,944 first described the isolation of an aqueous soluble proanthocyanidin polymer composition from *Croton* spp. and the use of the composition as an antiviral agent (See also Ubillas et al., 1994, Phytomedicine, 1:77). The proanthocyanidin polymer composition was shown to have antiviral activity against a variety of viruses including, respiratory syncytial, influenza, parainfluenza and herpes viruses. U.S. Pat. No. 5,211,944 also discloses the isolation of an aqueous soluble proanthocyanidin polymer composition from *Calophyllum inophyllum* and the use of this composition as an antiviral agent.

Exemplary proanthocyanidin polymer compositions useful in the methods presented herein are preferably isolated from a *Croton* spp. or *Calophyllum* spp. by any method known in the art. For example, the proanthocyanidin polymer composition may be isolated from a *Croton* spp. or *Calophyllum* spp. by the method disclosed in U.S. Pat. No. 5,211,944 or in Ubillas et al., 1994, Phytomedicine 1: 77-106.

In one specific embodiment, a proanthocyanidin polymer composition useful in the methods presented herein is crofelemer.

Crofelemer is an oligomeric proanthocyanidin extracted and purified from the red, viscous latex of the plant *Croton lechleri* of the family Euphorbiace. The plant is widely distributed throughout tropical Central America and South America and is widely recognized by ethnobotanists and local healers for its medicinal properties (McRae 1988), including for the treatment of diarrhea. Crofelemer is believed to exert its anti-diarrhea effect through luminal blockade of CFTR (cystic fibrosis transmembrane conductance regulator) chloride (Cl—) channel. Crofelemer has demonstrated in vitro activity against cholera toxin, forskolin, *E coli* LT and STa toxin-mediated Cl— secretion, and to normalize electrolyte and fluid accumulation in CT-treated mice (Gabriel 1999, Fischer 2004, Adam 2005) via its effects on the CFTR channel. Crofelemer also significantly improved the secretory diarrhea in humans due to enterotoxigenic *E. coli* (DiCesare 2002), which is also thought to evoke secretory diarrhea through activation of CFTR (Kunzelmann 2002). Blockade of the CFTR channel could be anticipated to have negative consequences in man, even mimicking cystic fibrosis. However, crofelemer has virtually no systemic bioavailability in humans. When studied, the results indicated that there was little or no absorption of crofelemer from the GI tract, and that crofelemer was well tolerated by normal male subjects. Thus, the site of action of crofelemer is topical in the gastrointestinal tract.

Crofelemer (CAS 148465-45-6) is an oligomeric proanthocyanidin of varying chain lengths derived from the Dragon's Blood *Croton lecheri* of the family Euphorbiaceae. Crofelemer has an average molecular weight of between approximately 1500 daltons and approximately 2900 daltons. The monomers comprising crofelemer comprise catechin, epicatechin, gallocatechin, and epigallocatechin. The chain length of crofelemer ranges from about 3 to about 30 units with an average chain length of about 8 units. The structure of crofelemer is shown below.

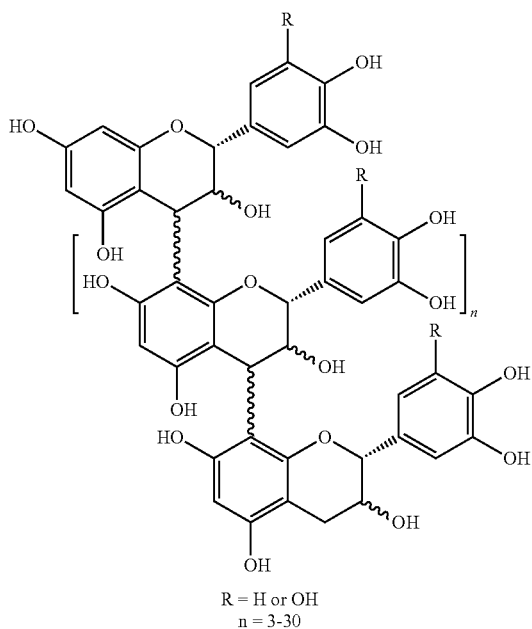

R = H or OH
n = 3-30

Wherein the average n=6.

Another method for isolating crofelemer can be found in U.S. Patent Publication No. 2005/0019389, the contents of which are expressly incorporated herein.

In addition, the proanthocyanidin polymer composition may be SB 300, as described, for example, by Fischer, H. et al., (2004, *J. Ethnopharmacol.*, 93(2-3):351-357). SB300 is a natural product extract that is particularly amenable for use in a non-enterically coated or protected formulations and compositions. In an embodiment, a pharmaceutically acceptable composition comprising a proanthocyanidin polymer from *Croton lechleri* and employed in the treatment methods of the invention can be obtained from *C. lechleri*, e.g., as described in WO 00/47062 to Shaman Pharmaceuticals, Inc., the contents of which are incorporated herein, and formulated as a food or dietary supplement or nutraceutical formulation, especially in a non-enterically coated formulation.

In other embodiments, a raw latex obtained from a *Croton* species or a *Calophyllum* species or an extract obtained from a *Croton* species or a *Calophyllum* species are useful in the methods presented herein. Exemplary extracts are described in Persinos et al., 1979, J. Pharma. Sci. 68:124 and Sethi, 1977, Canadian J. Pharm. Sci. 12:7.

B. Combinations with Chemotherapy Agents

The proanthocyanidins described herein may be combined with cancer drugs/chemotherapy agents for use in the methods described herein to treat CID. Cancer Drugs and Cancer Chemotherapeutic Agents are general terms with a meaning that includes the terms cancer drug, cancer chemotherapeutic drugs, cancer agent, cancer chemotherapy, chemotherapeutic drug, chemotherapeutic agent, chemotherapy, chemotherapy drug, cancer compound, cancer compound therapy, chemotherapy compound, and cancer drug therapies. Such chemotherapies shall also mean chemical substances that: may inhibit cancer cellular pathways; that may be used to kill cancer cells in vitro; that may be used to kill cancer cells in vivo, as in cancer tumors; and in some cases may be used to treat a person suffering cancer to protect viability of the cancer patient's normal cells or attack the viability of the cancer patient's cancer cells.

By way of serving only as examples without intending to limit the scope of the present invention, and to more particularly point out the practice of the present invention are the following examples and combination uses of the chemotherapy agents. A number of cellular pathways that may be targeted by chemotherapy agents are also listed. Generally a cancer chemotherapeutic drug is used in the form of a pharmaceutical composition, for a pharmaceutical use, or in a method of treatment of as patient.

Examples of cellular targets at which a cancer drug may have an effect are listed here, but are not limiting. The cellular targets of cancer chemotherapeutic agents include the following identified targets: mTORC, RAF kinase, MEK kinase, Phosphoinositol kinase 3, Fibroblast growth factor receptor, Multiple tyrosine kinase, Human epidermal growth factor receptor, Vascular endothelial growth factor, Other angiogenesis factors, Heat shock protein; Smo (smooth) receptor, FMS-like tyrosine kinase 3 receptor, Apoptosis protein inhibitor, Cyclin dependent kinases, Deacetylase, ALK tyrosine kinase receptor, Serine/threonine-protein kinase Pim-1, Porcupine acyltransferase, Hedgehog pathway, Protein kinase C, mDM2, Glypciin 3, ChK1, Hepatocyte growth factor MET receptor, Epidermal growth factor domain-like 7, Notch pathway, Src-family kinase, DNA methyltransferase, DNA intercalators, Thymidine synthase, Microtubule function disruptor, DNA cross-linkers, DNA strand breakers, DNA alkylators, JNK-dependent p53 Ser15 phosphorylation inducer, DNA topoisomerase inhibitors, Bcl-2, and free radical generators.

In various embodiments, the chemotherapy agent is selected from alkylating agents, anthracyclines, cytoskeletal disruptors (taxanes), epothilones, histone deacetylase inhibitors, inhibitors of topoisomerase I, inhibitors of topoisomerase II, kinase inhibitors, nucleotide analogs and precursor analogs, peptide antibiotics, platinum-based agents and retinoids.

In particular embodiments, the chemotherapy agent is a cancer growth inhibitor. Cancer growth inhibitors are a type of biological therapy and include tyrosine kinase inhibitors and HER2 inhibitors, proteasome inhibitors, mTOR inhibitors, PI3K inhibitors, histone deacetylase inhibitors and hedgehog pathway blockers.

In a particular embodiment, the chemotherapeutic agent is one or more tyrosine kinase inhibitors (TKI).

Tyrosine kinases are enzymes responsible for the activation of many proteins by signal transduction cascades. The proteins are activated by adding a phosphate group to the protein (phosphorylation). Tyrosine kinase inhibitors (TKI) are typically used as anti-cancer drugs. TKIs operate by four different mechanisms: they can compete with adenosine triphosphate (ATP), the phosphorylating entity, the substrate or both or can act in an allosteric fashion, namely bind to a site outside the active site, affecting its activity by a conformational change. TKIs are small molecular weight inhibitors of tyrosine phosphorylation, which do not inhibit protein kinases that phosphorylate serine or threonine residues and can discriminate between the kinase domains of the EGFR and that of the insulin receptor. It was further shown that in spite of the conservation of the tyrosine-kinase domains one can design and synthesize TKIs that discriminate between even closely related protein tyrosine kinases such as EGFR and its close relative HER2.

Specific examples of tyrosine kinase inhibitors include lapatinib, sunitinib, sorafenib, erlotinib, gefitinib, axitinib, imatinib, nilotinib, dasatinib, cabozantinib, ruxolitinib, neratinib, bosutinib and valatinib.

In a particular embodiment, the chemotherapeutic agent is one or more HER (Human epidermal growth factor receptor) inhibitors.

Signaling pathways activated by HER2 include: mitogen-activated protein kinase (MAPK), phosphoinositide 3-kinase (PI3K/Akt), phospholipase C γ, protein kinase C (PKC) and signal transducer and activator of transcription (STAT). Signaling through the ErbB family of receptors promotes cell proliferation and opposes apoptosis, and therefore must be tightly regulated to prevent uncontrolled cell growth from occurring. Amplification or over-expression of the ERBB2 gene is strongly associated with increased disease recurrence and a poor prognosis. Over-expression is also known to occur in breast, ovarian, stomach, and aggressive forms of uterine cancer, such as uterine serous endometrial carcinoma. HER2 is co-localized, and, most of the time, co-amplified with the gene GRB7, which is a proto-oncogene associated with breast, testicular germ cell, gastric, and esophageal tumors. HER2 proteins have been shown to form clusters in cell membranes that may play a role in tumorigenesis. Specific examples of HER (human epidermal growth factor receptor) inhibitors include RG7116, RG1273 (pertuzumab, Perjeta®), RG3502 (trastuzumab emantasine, T-DMI), RG597 (trastuzumab, HERCEPTIN), RGA201 (RG7160), erlotinib (Tarceva®), dacomitinib (PF-00299804), PF-05280014 (Pfizer's biosimilar mAB to RG597).

Generic names of cancer chemotherapeutic drugs that have been typically used in cancer patients include: doxorubicin, epirubicin; 5-fluorouracil, paclitaxel, docetaxel, cisplatin, bleomycin, melphalan, plumbagin, irinotecan, mitomycin-C, and mitoxantrone. By way of example, some other cancer chemotherapeutic drugs that may be used and may be in stages of clinical trials include: resminostat, tasquinimod, refametinib, lapatinib, Tyverb, Arenegyr, pasireotide, Signifor, ticilimumab, tremelimumab, PrevOnco, ABT-869, linifanib, tivantinib, Tarceva, erlotinib, Stivarga, regorafenib, fluoro-sorafenib, brivanib, liposomal doxorubicin, lenvatinib, ramucirumab, peretinoin, Ruchiko, muparfostat, Teysuno, tegafur, gimeracil, oteracil, and orantinib.

Examples of FDA approved cancer drugs (by generic name) which can be used in the present invention include: sorafenib, regorafenib, imatinib, eribulin, gemcitabine, capecitabine, pazopanib, lapatinib, dabrafenib, sunitinib malate, crizotinib, everolimus, torisirolimus, sirolimus, axitinib, gefitinib, anastrozole, bicalutamide, fulvestrant, ralitrexed, pemetrexed, goserilin acetate, erlotinib, vemurafenib, visiodegib, tamoxifen citrate, paclitaxel, docetaxel, cab azitaxel, oxaliplatin, ziv-aflibercept, bevacizumab, trastuzumab, pertuzumab, pantiumumab, taxane, bleomycin, melphalan, plumbagin, camptosar, mitomycin-C, doxorubicin, pegylated doxorubicin, 5-fluoro-uracil, temozolomide, pasireotide, tegafur, gimeracil, oteraci, bortezomib, lenalidomide, and romidepsin.

Manufacturer brand names for some cancer drugs that may be used in the present invention include: NEXAVAR (sorafenb), STIVARGA (regorafenib), AFINITOR (everolimus), GLEEVEC (imatinib), HALAVEN (eribulin), ALIMTA (pemetrexed), GEMZAR (gemcitabine), VOTRIENT (pazopanib), TYKERB (lapatinib), TAFINIAR (dabrafenib), SUTENT (sutinib malate), XALKORI (crizotinib), TORISEL (torisirolimus), INLYTA (axitinib), IRESSA (gefitinib), ARIMIDEX (anastrole), CASODEX (bicalutamide), FASLODEX (fulvestrant), TOMUDEX (ralitrexed), ZOLADEX (goserilin acetate), TARCEVA (erlotininb), XELODA (capecitabine), ZELBROF (vemurafenib), ERIVEDGE (visiodegib), PERJETA (pertuzumab), HERCEPTIN (trastuzumab), TAXOTERE (docetaxel), JEVTANA (cabazitaxel), ELOXATIN (oxaliplatin), ZALTRAP (ziv-aflibercept), AVASTIN (bevacizumab) Nolvadex, Istubal, and VALODEX (tamoxifen citrate), TEMODAR (temozolomide), SIGNIFOR (pasireotide), VECTIBIX (pantiumumab), ADRIAMYCIN (doxorubicin), DOXIL (pegylated doxorubicin), ABRAXANE (Paclitaxel), TEYSUNO (tegafur, gimeracil, oteracil), BORTEZOMIB (Velcade) and with lenalidomide, ISTODAX (romidepsin).

Cancer drug therapies contemplated for the present invention include Iressa (gefitinib), Arimidex (anastrole), Casodex (bicalutamide), Faslodex (fulvestrant), Tomudex (ralitrexed), Zoladex (goserilin acetate), Nolvadex, Istubal, and Valodex (tamoxifen citrate), Erbitux (cetuximab), Sprycel (dasatinib), Ixempra (ixabepilone), Taxol (paclitaxel), Paraplatin (carboplatin), and Yervoy (ipilumumab), Vectibix (pantiumumab, rilotumumab, trebananib, blinatumumab, Halaven (eribulin), Alimta (pemetrexed), and Gemzar (gemcitabine), Votrient (pazopanib), Tykerb (lapatinib), and Tafiniar (dabrafenib). Doxil (doxorubicin, adriamycin), Temodar (temozolomide), Afinitor (everolimus), Gleevec (imatinib), and Signifor (pasireotide), dovitinib, midostaurin, panobinostat, Teysuno (tegafur, gimeracil, oteracil), navitoclax, velipariban, linifanib, thrombospondin, ilorasertib, elagolix, atrasentan, Sutent (sutinib malate), Xalkori (crizotinib), Torisel (torisirolimus), Inlyta (axitinib), dacomitinib, bosutinib, Tarceva (erlotininb), Xeloda (capecitabine), Zelbrof (vemurafenib), Erivedge (visiodegib), Perj eta (pertuzumab), Herceptin (trastuzumab) Avastin (bevacizumab), Taxotere (docetaxel), Jevtana (cabazitaxel), Eloxatin (oxaliplatin), Zaltrap (ziv-aflibercept), iniparib, neratinib (HKI-272) and ombrabulin.

III. Methods of Treatment

Provided herein are methods of treating, preventing, or alleviating diarrhea or gastrointestinal symptoms caused by chemotherapy comprising administering to a subject in need thereof an effective amount of crofelemer alone or in combination with a chemotherapy agent. Exemplary diarrhea that can be treated or prevented using the methods presented herein include CID. The subject is preferably a human.

In one embodiment, treating CID includes an improvement of the following symptoms of CID, including, for example, a decrease in the number of bowel movements per day (frequency), a decrease in the number of watery bowel movements per day, a decrease in symptom frequency (urgency, fecal incontinence), a decrease in symptom severity (abdominal pain or discomfort), a decrease in daily stool consistency score (watery to formed), or a decrease in stool consistency leading to formed stools from watery stools. In certain embodiments, the treatment results in a reduction in the Grade of the Common Toxicity Criteria for diarrhea, for example, from Grade 4, to Grade 3, Grade 2 or Grade 1; or from Grade 3, to Grade 2 or Grade 1; or from Grade 2 to Grade 1. In certain embodiments, the treatment results in an improvement such that the subject does not meet any of the Common Toxicity Criteria Grades, i.e., is no longer suffering from diarrhea.

In other specific embodiments, treatment can also include, for example, one or more of a decrease in the number of bowel movements per day, a decrease in the number of watery bowel movements per day, an improvement in the daily abdominal score for pain or discomfort, an improvement in the score for daily stool consistency, a decrease in the number of days per week or per month that subjects experienced urgency, or a decrease in the number of days per week or per month that subjects experienced fecal incontinence.

In one aspect, provided herein are methods of treating CID in a subject undergoing chemotherapy comprising administering to a subject in need thereof a composition comprising an effective amount of crofelemer to treat CID. In specific embodiments, the crofelemer is an enterically coated oral dosage form. In other embodiments, the crofelemer is an oral dosage form that is not enterically protected.

In one embodiment, the crofelemer is administered at the same time as chemotherapy to reduce or delay the onset of CID. In one embodiment, the crofelemer is administered before chemotherapy to reduce or delay the onset of CID. In one embodiment, the crofelemer is administered after chemotherapy to reduce the onset of or treat CID.

CID can be an adverse side effect of chemotherapy, particularly chemotherapy for treatment of cancer. In some embodiments, CID can be severe enough to interfere with the chemotherapy regimen of the subject because of lack of tolerance or reduced tolerance for the chemotherapy regimen due to the CID. In certain embodiments, therefore, provided are methods of increasing the tolerance of a subject for a certain chemotherapy agent or regimen such that the subject can tolerate and can be administered a recommended dosage of a chemotherapeutic agent or can be administered a chemotherapeutic agent.

In some embodiments, the subject is undergoing chemotherapy to treat one or more forms of cancer. The one or more forms of cancer can be selected from breast cancer, ovarian cancer, prostate cancer, bladder cancer, cervical cancer, uterine cancer, testicular cancer, kidney cancer, thyroid cancer, oral or oropharyngeal cancer, astrocytoma, sarcoma, mesothelioma, meningioma, lymphoma, myeloma, head and neck cancer, lung cancer, carcinoma (e.g., squamous cell carcinoma), malignant melanoma, peritoneal cancer, gastric cancer, hepatic cancer, colorectal cancer, gallbladder cancer, bone cancer, pancreatic cancer, tongue cancer, esophageal cancer, brain tumor, brain stem glioma, a metastases thereof, and leukemia.

In one embodiment, the chemotherapy comprises one or more tyrosine kinase inhibitors.

In one embodiment, the tyrosine kinase inhibitor is selected from lapatinib, sunitinib, sorafenib, erlotinib, gefitinib, axitinib, imatinib, nilotinib, dasatinib, cabozantinib, ruxolitinib, neratinib, bosutinib, toceranib, and valatinib.

In one embodiment, the chemotherapy comprises one or more HER (Human epidermal growth factor receptor) inhibitors.

In one embodiment, the HER (Human epidermal growth factor receptor) inhibitor is selected from RG7116, RG1273 (pertuzumab, Perjeta®), RG3502 (trastuzumab emantasine, T-DMI), RG597 (trastuzumab, HERCEPTIN), RGA201 (RG7160), erlotinib (Tarceva®), dacomitinib (PF-00299804), PF-05280014 (Pfizer's biosimilar mAB to RG597).

In various embodiments, the crofelemer is administered after a subject begins to exhibit symptoms of CID. In various embodiments, the crofelemer is administered prior to the start of chemotherapy or of a round of chemotherapy to prevent or reduce the severity of CID associated with the chemotherapy. In embodiments, the crofelemer is administered for one day, three days, or one week prior to chemotherapy or a round of chemotherapy to prevent or reduce the risk or incidence of CID upon treatment of chemotherapy.

In certain embodiments, the crofelemer is administered for the duration of treatment with the chemotherapy. The duration of treatment can comprise the time between two chemotherapy rounds. For example, in certain embodiments, chemotherapy is administered once every three weeks or four weeks or once every 15, 16, 17, 18, 19, 20, 21, 22, 23, 24, 25, 26, 27, 28, 29, 30, 31, 32, 33, 34, or 35 days.

In certain embodiments, the crofelemer is administered until symptoms of CID are ameliorated and then crofelemer is discontinued.

As will be readily apparent to one skilled in the art, the useful in vivo dosage to be administered and the particular mode of administration may vary depending upon the age, weight and mammalian species treated, the particular compounds employed, and/or the specific use for which these compounds are employed. The determination of effective dosage levels, that is the dosage levels necessary to achieve the desired result, can be accomplished by one skilled in the art using routine pharmacological methods and in consultation with the data presented herein.

In one aspect, provided herein are methods of treating stool consistency in a subject undergoing chemotherapy, wherein a subject is considered treated if there is an improvement in the score for daily stool consistency and/or a decrease in stool consistency score a measured throughout the day or days or weeks comprising administering to a subject in need thereof a composition comprising an effective amount of crofelemer to treat stool consistency. This decrease may be measured from a baseline. The baseline may be determined in the days to week prior to treatment with crofelemer. Treatment comprises administering about 250 mg to about 1000 mg per day; administering about 250 mg per day; administering 1000 mg per day; administering about 125 mg two times per day; or administering about 500 mg two times per day of crofelemer, preferably an enteric coated oral dosage form, to a subject in need thereof or a dosage of a proanthocyanidin polymer composition (including a non-enteric protected oral dosage form of crofelemer) that is bioequivalent to 250 mg to about 1000 mg per day; about 250 mg per day; 1000 mg per day; about 125 mg two times per day; or about 500 mg two times per day of enteric protected oral dosage form of crofelemer.

In one aspect, provided herein are methods of alleviating watery diarrhea in a subject undergoing chemotherapy, wherein a subject is considered treated if the subject experiences a decrease in the number of watery bowel movements per day and/or over days, a week or weeks of administration of crofelemer comprising administering to a subject in need thereof a composition comprising an effective amount of crofelemer to alleviate watery diarrhea.

This decrease may be measured from a baseline. The baseline may be determined in the days to week prior to treatment with crofelemer. Treatment comprises administering about 250 mg to about 1000 mg per day; administering about 250 mg per day; administering 1000 mg per day; administering about 125 mg two times per day; or administering about 500 mg two times per day of crofelemer, preferably an enteric coated oral dosage form of crofelemer, to a subject in need thereof, or, alternatively, a dosage of a proanthocyanidin polymer composition (including a non-enteric protected oral dosage form of crofelemer) that is bioequivalent to 250 mg to about 1000 mg per day; about 250 mg per day; 1000 mg per day; about 125 mg two times per day; or about 500 mg two times per day of enterically protected oral dosage form of crofelemer.

In one aspect, presented herein are methods a decreasing the number of bowel movements per day, wherein a subject is considered treated if there is a decrease in the number of bowel movements per day as measured from a baseline comprising administering to a subject in need thereof a composition comprising an effective amount of crofelemer to decrease the number of bowel movements per day.

The baseline may be determined in the days to week prior to treatment with crofelemer. Treatment comprises administering about 250 mg to about 1000 mg per day; administering about 250 mg per day; administering 1000 mg per day; administering about 125 mg two times per day; or administering about 500 mg two times per day of crofelemer, preferably an enteric coated oral dosage form of crofelemer, to a subject in need thereof, or, alternatively, a dosage of a proanthocyanidin polymer composition (including a non-enteric protected oral dosage form of crofelemer) that is bioequivalent to 250 mg to about 1000 mg per day; about 250 mg per day; 1000 mg per day; about 125 mg two times per day; or about 500 mg two times per day of enterically protected oral dosage form of crofelemer.

In certain embodiments, the methods provided result in a decrease in the Grade of Common Toxicity Criteria Grades for diarrhea. In addition, the methods provided result in increased ability to tolerate the chemotherapeutic regimen such that the subject remains on and is compliant with the prescribed chemotherapeutic regimen.

Crofelemer may be administered, for example, once a day, twice a day, three times a day, or four times or more often as necessary per day. Crofelemer may be administered in doses, for example of from about between 25 mg BID to about 3000 mg TID, preferably crofelemer is administered from between about 125 mg to about 1000 mg per day. In another embodiment, crofelemer is administered between 125 mg BID to about 500 mg BID depending of symptoms. In another embodiment, crofelemer is administered as 125 mg BID. In another embodiment, crofelemer is administered as 500 mg BID. Crofelemer may be administered orally, for example, in tablet form, powder form, liquid form or in capsules. In preferred embodiments, the crofelemer is formulated as an enteric coated oral dosage form. In other embodiments, the crofelemer is an oral dosage form that is not enteric coated.

In exemplary embodiments, the subject is orally administered 250, 500, or 1000 mg/day of enteric protected crofelemer or is administered a dose of a proanthocyanidin polymer composition, including crofelemer, that is bioequivalent to an oral dosage form of enteric coated crofelemer administered at 250, 500, or 1000 mg/day.

In specific embodiments, the subject is administered 125, 250 or 500 mg p.o. b.i.d (orally twice per day) enteric coated crofelemer or a dosage of a proanthocyanidin polymer composition bioequivalent to 125, 250 or 500 mg p.o. b.i.d enteric coated crofelemer. Other appropriate dosages for methods may be determined by health care professionals or by the subject. The amount of crofelemer administered daily may be increased or decreased based on the weight, age, health, sex or medical condition of the subject. One of skill in the art would be able to determine the proper dose for a subject based on this disclosure and the data presented in the Examples, which follow.

In other embodiments, the subject is treated with crofelemer for 2, 4, 6, 8, 10, 12, 14, 16, 18, 20, 22, 24 or more weeks or 26 or more weeks. Length of treatment may vary depending on the type and length of disease and the proper length of treatment may be easily determined by one of skill in the art having the benefit of this disclosure.

Subjects in need thereof include subjects having or that are susceptible to or who have CID.

In certain embodiments, the subject is administered crofelemer for treatment of CID in combination with one or more anti-diarrheals, such as, but not limited to, loperamide, octreotide, probiotics and any other agent useful for the treatment of chemotherapy associated diarrhea.

IV. Pharmaceutical Preparations

Also provided herein are pharmaceutical compositions, comprising an effective amount of a crofelemer described herein and a pharmaceutically acceptable carrier. In a further embodiment, the effective amount is effective to treat CID.

Examples of the preparation and use of crofelemer have been described in U.S. Pat. No. 7,556,831, US Patent Publication 20070254050 and US Patent Publication 20080031984, all of which are incorporated herein by reference in their entirety.

One embodiment includes pharmaceutical compositions comprising crofelemer and a pharmaceutically acceptable carrier. In preferred embodiments, the pharmaceutical composition is an enterically protected oral dosage form, such as a tablet or capsule. Alternatively, the pharmaceutical composition is an oral dosage form that is not enterically protected.

The pharmaceutical compositions described herein may further comprise excipients, for example, one or more of a diluting agent, binding agent, lubricating agent, disintegrating agent, coloring agent, flavoring agent or sweetening agent. Compositions may be formulated for selected coated and uncoated tablets, hard and soft gelatin capsules, sugar-coated pills, lozenges, wafer sheets, pellets and powders in sealed packet. For example, compositions may be formulated for topical use, for example, ointments, pomades, creams, gels and lotions.

In certain embodiments, these pharmaceutical compositions are suitable for topical or oral administration to a subject. In other embodiments, as described in detail below, the pharmaceutical compositions may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

A pharmaceutical carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch;

(3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Compositions containing crofelemer include those suitable for oral, nasal, topical (including buccal and sublingual), rectal, vaginal, aerosol and/or parenteral administration. The compositions may conveniently be presented in unit dosage form and may be prepared by any methods known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.01% to about 99% of active ingredient, for example, from about 5% to about 70%, or from about 10% to about 30%.

Liquid dosage forms for oral or rectal administration of crofelemer may include, for example, pharmaceutically-acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Suspensions, in addition to crofelemer may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof. Dosage forms for the topical or transdermal administration of crofelemer can include, for example, powders, sprays, ointments, pastes, creams, lotions, gels, solutions, patches and inhalants. The ointments, pastes, creams and gels may contain, in addition to crofelemer, excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to a crofelemer, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Examples of suitable aqueous and non-aqueous carriers which may be employed in the pharmaceutical compositions can include, for example, water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

In one embodiment, crofelemer is enteric coated so as to protect it from degradation by the acidic conditions of the stomach and/or from interactions with proteins, such as pepsin, present in the stomach, e.g., an enteric protected formulation. In a specific embodiment, crofelemer is in tablet form. In yet another embodiment, the tablet is enteric coated, e.g., Eudragit®. In one embodiment, crofelemer is formulated as an enteric coated bead or granule in an enteric coated capsule shell. In another embodiment, crofelemer is formulated in a delayed release composition.

In certain embodiments, the composition is formulated with a compound or compounds which neutralize stomach acid. Alternatively, the pharmaceutical composition containing the composition is administered either concurrent with or subsequent to or after administration of a pharmaceutical composition which neutralize stomach acid. Compounds, such as antacids, which are useful for neutralizing stomach acid include, but are not limited to, aluminum carbonate, aluminum hydroxide, bismuth subnitrate, bismuth subsalicylate, calcium carbonate, dihydroxyaluminum sodium carbonate, magaldrate, magnesium carbonate, magnesium hydroxide, magnesium oxide, and mixtures thereof. Compounds that are able to reduce the secretion of stomach acid and/or are able to reduce the acidity of stomach fluid are well known in the art and include, but are not limited to, antacids (aluminum hydroxide, aluminum carbonate, aluminum glycinate, magnesium oxide, magnesium hydroxide, magnesium carbonate, calcium carbonate, sodium bicarbonate), stomach acid blockers and a combination of any of the foregoing. In general, any drug that has been approved for sale by the relevant government agency and is able to reduce the production of stomach acid and/or reduce the acidity of stomach fluid can be administered in combination with an inhibitor molecule, such as crofelemer, in accordance with the methods presented herein.

In a particular embodiment where crofelemer is not enteric coated, crofelemer is formulated with one or more compounds that are able to reduce the secretion of stomach acid and/or able to reduce the acidity of stomach fluid. In an exemplary embodiment, crofelemer is formulated in a controlled release (delayed release) composition, such as Merck GEM, Alza OROS, wax matrix (release is primarily delayed until after the formulation passes out of the stomach and into the intestine).

Also provided herein are pharmaceutical formulations of crofelemer comprising the composition along with a pharmaceutically acceptable carrier, at a dose which is therapeutically effective at treating CID. In one embodiment, a directly compressible crofelemer (e.g., that can be directly compressed, without excipients, into a tablet of pharmaceutically acceptable hardness and friability) compressed into a tablet, optionally with a lubricant, such as but not limited to magnesium stearate, is enteric coated. These formulations can be prepared by methods known in the art, see, e.g. methods described in Remington's Pharmaceutical Sciences, 18th Ed., ed. Alfonso R. Gennaro, Mack Publishing Co., Easton, Pa., 1990.

In a specific embodiment, the proanthocyanidin polymer composition comprises crofelemer (CAS 148465-45-6).

In a more another embodiment, a composition is enteric coated. Enteric coatings are those coatings that remain intact in the stomach, but will dissolve and release the contents of the dosage form once it reaches the small intestine. A large number of enteric coatings are prepared with ingredients that have acidic groups such that, at the very low pH present in the stomach, i.e. pH 1.5 to 2.5, the acidic groups are not ionized and the coating remains in an undissociated, insoluble form. At higher pH levels, such as in the environment of the intestine, the enteric coating is converted to an ionized form, which can be dissolved to release the inhibitor molecule. Other enteric coatings remain intact until they are degraded by enzymes in the small intestine, and others break apart after a defined exposure to moisture, such that the coatings remain intact until after passage into the small intestines.

Polymers which are useful for the preparation of enteric coatings include, but are not limited to, shellac, starch and amylose acetate phthalates, styrene-maleic acid copolymers, cellulose acetate succinate, cellulose acetate phthalate (CAP), polyvinylacetate phthalate (PVAP), hydroxypropylmethylcellulose phthalate (grades HP-50 and HP-55), ethylcellulose, fats, butyl stearate, and methacrylic acid-methacrylic acid ester copolymers with acid ionizable groups. In one embodiment, the pharmaceutical composition contains a polymeric proanthocyanidin composition and the enteric coating polymer Eudragit® L 30D, an anionic copolymer of methacrylic acid and methyl acrylate with a mean molecular weight of 250,000 Daltons. In another embodiment, the enteric coating polymer is Eudragit® L 30D-55. Application of the enteric coating to the crofelemer composition can be accomplished by any method known in the art for applying enteric coatings. For example, but not by way of limitation, the enteric polymers can be applied using organic solvent based solutions containing from 5 to 10% w/w polymer for spray applications and up to 30% w/w polymer for pan coatings. Solvents that are commonly in use include, but are not limited to, acetone, acetone/ethyl acetate mixtures, methylene chloride/methanol mixtures, and tertiary mixtures containing these solvents. Some enteric polymers, such as methacrylic acid-methacrylic acid ester copolymers can be applied using water as a dispersant. The volatility of the solvent system must be tailored to prevent sticking due to tackiness and to prevent high porosity of the coating due to premature spray drying or precipitation of the polymer as the solvent evaporates.

In another embodiment, the pharmaceutical composition comprising crofelemer is formulated as enteric coated granules or powder (microspheres with a diameter of 300-5001) provided in either hard shell gelatin capsules or suspended in an oral solution for pediatric administration. The enteric coated powder or granules may also be mixed with food, particularly for pediatric administration.

The granules and powder can be prepared using any method known in the art, such as but not limited to, crystallization, spray-drying or any method of comminution, for example, using a high speed mixer/granulator. Exemplary formulations may be found, for example, in the following US patents and applications U.S. Pat. No. 7,341,744; U.S. Ser. Nos. 11/510,152; and 12/175,131.

Regardless of the route of administration selected, crofelemer is formulated into pharmaceutically-acceptable dosage forms by methods known to those of skill in the art.

In combination therapy treatment, both the compounds and the other drug agent(s) are administered to mammals (e.g., humans, male or female) by methods known in the art. The agents may be administered in a single dosage form or in separate dosage forms. Effective amounts of the other therapeutic agents are well known to those skilled in the art. However, it is well within the skilled artisan's purview to determine the other therapeutic agent's optimal effective-amount range. In one embodiment in which another therapeutic agent is administered to an animal, the effective amount of the compound is less than its effective amount in case the other therapeutic agent is not administered. In another embodiment, the effective amount of the agent is less than its effective amount in case the compound is not administered. In this way, undesired side effects associated with high doses of either agent may be minimized. Other potential advantages (including without limitation improved dosing regimens and/or reduced drug cost) will be apparent to those skilled in the art.

In various embodiments, the therapies (e.g., prophylactic or therapeutic agents) are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In one or more embodiments, two or more therapies are administered within the same patient's visit.

V. Kits

Kits are also provided herein, for example, kits for treating a diarrhea, e.g., CID in a subject undergoing chemotherapy. The kits may contain, for example, crofelemer or a pharmaceutical composition comprising crofelemer and instructions for use. The instructions for use may contain prescribing information, dosage information, storage information, and the like.

Label instructions include, for example, instructions to take the crofelemer for at least 3 days for the treatment of CID. The instructions could also read, for example, take from between 125 mg BID to 500 mg BID of crofelemer until resolution of symptoms or for the duration of chemotherapy treatment for treatment of CID. The instructions could also read, for example, take 125 mg BID of crofelemer until resolution of symptoms or for the duration of chemotherapy treatment for treatment of CID. The instructions could also read, for example, take 500 mg BID of crofelemer until resolution of symptoms of CID.

EXAMPLE

It should be appreciated that the invention should not be construed to be limited to the example, which is now described; rather, the invention should be construed to include any and all applications provided herein and all equivalent variations within the skill of the ordinary artisan.

Example 1: A Study of the Safety and Effectiveness of Crofelemer for the Treatment of Chemotherapy-Induced Diarrhea in Dogs Toceranib phosphate (Palladia®) is a multi-kinase inhibitor targeting several receptor tyrosine kinases (RTK), and is indicated for the treatment of Patnaik grade II or III, recurrent, cutaneous mast cell tumors with or without regional lymph node involvement in dogs. Toceranib phosphate is currently used more often off-label to treat neoplasias other than mast cell tumors.

Toceranib phosphate is indicated at an initial dosage of 3.25 mg/kg (1.48 mg/lb) body weight, orally every other day. Dose reduction intervals of 0.5 mg/kg [to a minimum dose of 2.2 mg/kg (1.0 mg/lb) every other day] and dose interruptions (cessation of toceranib phosphate for up to two weeks) may be utilized, if needed, to manage adverse reactions. This approval was based upon a randomized, placebo-controlled, double-masked, multicenter clinical field study showing a statistically significant advantage for toceranib phosphate over placebo (37% vs. 8%, p<0.001) in the primary effectiveness endpoint of objective response at the end of the six-week masked phase (London C A, et al., Clin Cancer Res, 15(11), 2009). Toceranib phosphate is sometimes prescribed at a lower dose (2.5-3 mg/kg/dose) than the labeled dose; however, adverse effects of diarrhea are still observed, although generally with a lower frequency.

It is not expected that any increase in adverse reactions would be noted with the combination of crofelemer and toceranib phosphate over toceranib phosphate alone, since crofelemer is minimally absorbed and has been demonstrated in human studies to have minimal interaction on pharmacologic exposure of other drugs.

Toceranib phosphate has been associated with severe diarrhea or GI bleeding that requires prompt treatment. During the masked phase of the London study, 46% all grade and 7% grade 3-4 diarrhea was observed on toceranib phosphate vs. 27% all grade and 3% grade 3-4 diarrhea on placebo. During the masked plus open label phases of the study, 59% any grade and 8% grade 3-4 diarrhea was observed with toceranib phosphate. Dose interruptions and dose reductions are considered necessary depending upon the severity of clinical signs.

Crofelemer (SP-303) is a proanthocyanidin molecule purified from the tree *Croton lechleri* that has strong antisecretory properties and a unique mode of action through modulation and normalization of hyperactivity of both cAMP-stimulated CFTR channels and calcium-activated chloride channels (CaCC). Crofelemer treats diarrhea without affecting intestinal motility in several species including dogs and humans. Crofelemer is not absorbed systemically at the therapeutic dose, but instead acts locally within the lumen of the gastrointestinal tract.

Crofelemer is approved by the FDA (CDER) for the treatment of non-infectious diarrhea in humans with HIV who are being treated with anti-retrovirals. The approval supports chronic administration of crofelemer.

Crofelemer is being studied to treat acute diarrhea in dogs. In a proof-of-concept study (CANA-001), crofelemer (2-4 mg/kg twice daily for three days; n=29) or placebo (twice daily for three days; n=32) was administered to dogs exhibiting acute diarrhea. After three 24-hour treatment periods and one 24-hour observation period, dogs treated with crofelemer had better resolution of diarrhea than did placebo-treated dogs. An ongoing randomized, placebo-controlled study (CANA-003) is designed to provide substantial evidence of effectiveness of crofelemer for acute diarrhea in dogs.

A safety and tolerability study of crofelemer dosed at 2-4 mg/kg BID for three days was performed in eight dogs on chemotherapy (CANA-002). This was a two-site, open-label, safety study of crofelemer enteric-coated tablet in client-owned dogs with current (active) diarrhea or a history of CID within 90 days prior to screening (either by previously prescribed medications to treat diarrhea or by signs noted in their medical chart). No serious adverse events (SAEs) were reported during the study, and no subjects withdrew from the study for any reason including AEs or subject safety concerns. No clinically significant safety findings were observed during the study. All eight dogs had a formed stool at the last reported observation.

Study Design

This study is a prospective, double-blinded, multi-site proof-of-concept study (Table 1).

TABLE 1

Summary of C-102 experimental design

| Group | N | Treatment | Dose (mg/kg/dose) | Route | Frequency | Number of Doses |
|---|---|---|---|---|---|---|
| IVP | ≥25 | Crofelemer | 2-54.3 | PO | BID | 6 doses |
| CP | ≥12 | Placebo | 0 | PO | BID | 6 doses |

Study Overview

This study will be conducted on an out-patient basis, sourcing dogs from referral and academic veterinary centers. A single protocol will be followed at all study sites. Only dogs that have received a minimum of three doses of Palladia® brand name tablets manufactured by Zoetis will be eligible for this study. Due to the possibility that compounded toceranib phosphate may cause more variation in the induction of diarrhea and cause more severe diarrhea, dogs taking compounded toceranib phosphate are not eligible for this study. Palladia® brand name tablets may be obtained from any source that is agreeable to the Investigator and may include the hospital or site pharmacy, a local pharmacy or an online pharmacy.

Dogs exhibiting diarrhea with a Purina Fecal Score (PFS) of 6 or 7 will be presented by their owner for enrollment in the study. Owners may be informed about this clinical trial at the time their dog begins Palladia® or within approximately 1-12 weeks of starting Palladia®, although only 20-40% of dogs treated with Palladia® will develop clinically significant diarrhea, depending upon dosing. If their dog does develop clinically significant diarrheal signs while taking Palladia®, the owner will be instructed to take a photo of the diarrhea with their cell phone camera and then present their dog for a physical exam. If the Investigator assesses the dog as meeting the enrollment criteria for the study, enrollment will occur.

Baseline information will include the qualifying PFS (and any photos that the owner has), the time that diarrhea was first noted, the number of diarrhea episodes since the diarrhea began (if known), review of concomitant medications within 72 hours prior to enrollment, medical and medication history, physical examination and collection of samples for clinical pathology testing (CBC, CHEM, U/A, fecal sample for ova and parasites). Dogs meeting all of the inclusion criteria and none of the exclusion criteria will be randomized to receive either the Investigational Veterinary Product (IVP) or Control Product (CP) twice daily (12±2 hours apart) for a total of 6 doses. The first dose should be administered orally in the hospital by the hospital staff immediately following completion of all the screening activities (i.e., the same day).

The Study Period (T0-T96 hr) is divided into three 24-hour Treatment Periods (T0-T24 hr; T>24 hr-T48 hr; T>48 hr-T72 hr) followed by a 24-hour Observation Period (T>72 hr-T96 hr), which begins 12 hours following the last treatment (administered at T60 h) and continues for 24 hours. Therefore, each dog will be assessed by the owner for a total of 96 hours. Dosing for each dog occurs approximately at T0, T12 hr, T24 hr, T36 hr, T48 hr and T60 hr. During the Study Period, dogs live at home, and the safety and health of the dogs will be monitored by their owner with daily phone calls between the Investigator or trained designee. These daily calls assess the health status of the dog and ensure that the dog is brought to the Investigator to assess for any possible adverse events.

Fecal Assessments are completed daily by the owner. Owners are asked to complete a daily diary in which they record the time, the color and one photo of each bowel movement (all elimination within a 15-minute timeframe will be considered a single bowel movement). This allows a single blinded person, to select the appropriate Purina Fecal Score for each bowel movement. Abnormal observations will be reported by the owner which will be assessed by the Investigator or trained designee each day for determination of Adverse Events. Concomitant medications will be reported by the owner and recorded by the study staff during the 96-hour Study Period.

At the end of the Study Period or at discontinuation, dogs will undergo a final evaluation by the Investigator before completing the study, which will include another physical examination and additional clinical pathology testing (CBC, CHEM). A repeat UA is conducted only if the baseline results were abnormal.

Data is captured on electronic data capture forms, with paper forms used as a backup.

Study Procedures

Informed Consent

Owners are approached by their dog's treating veterinarian/Investigator about participation in this study. Diarrhea associated with Palladia® therapy typically occurs within the first few weeks of starting therapy. Therefore, owners may be approached about this study at the time their dog is started on Palladia® treatment of a malignancy, or within 90 days of starting Palladia® treatment. This study may be discussed with the dog owner in anticipation of the dog potentially developing diarrhea, with the understanding that many of these dogs will not develop signs of diarrhea and ultimately will not be enrolled in the study. Alternatively, an owner may be presented with this study at the time of first presenting with their dog that already has diarrheal signs. Owners are instructed to take a photo of the diarrhea with their cellular telephone or digital camera. The owners are provided with written and oral information about the study at that time. If an owner agrees to have their dog participate in the study, at the time their dog develops diarrhea per the study requirements, the owner will sign and date an informed consent form (ICF) prior to screening activities.

Screening

If an owner notes that his/her dog has developed diarrhea after a minimum of three doses of Palladia® brand name tablets, the owner will bring the dog to the study site and the owner and Investigator will discuss the PFS chart and review any photos of diarrhea that the owner may have. If the screening PFS is a 6 or 7, an informed consent must be obtained, and then the Investigator will determine if the dog meets the study inclusion and exclusion criteria. The VCOG-CTCAE v1.1 Grade for diarrhea (See Appendix 4) will also be captured at screening. Upon verifying that a dog meets the inclusion criteria and none of the exclusion criteria of the study, a medical history, assessment of previous and current medications, physical exam and collection of samples for clinical chemistry, hematology, urinalysis and fecal analysis will be obtained to establish pre-treatment (baseline) values. Results of the above baseline laboratory assessments will not preclude a dog from being enrolled unless the dog does not meet the inclusion and exclusion criteria of the protocol. Instead, pre-treatment values will be considered baseline findings and recorded on the appropriate CRF.

Time 0

After the dog has passed screening it is considered eligible for enrollment and is enrolled in the study. The first dose of the study treatment will be administered orally to the dog by the study staff while the dog is still at the study site. The time point for this first dose administration will be recorded and noted as Time 0 (T0). Since dosing is intended to occur approximately every 12 hours, the second dose will be administered at home by the owner on the same day if the first dose was administered before 12 noon, or on the following morning if the first dose was administered in the afternoon. All subsequent doses will follow the twice daily 12±2 hours apart dosing schedule.

Treatment Period

Study treatments will be administered orally during the Treatment Period (T0 hr-T72 hr) twice daily (12±2 hours apart) for three 24-hour Treatment Periods. However, the second dose may be administered up to 18 hours after the first dose if the first dose was administered at the study site during the afternoon. A vehicle such as a Greenies Pill Pocket™ may be used for dosing but is not required. Study dogs must remain on Palladia® brand name tablets and not change to compounded toceranib phosphate while on study.

For each bowel movement noted, the dog owner or his/her designee will take a photo and upload it to a server throughout the subsequent 96 hours from the first dose. If the owner/designee finds that a study dog has had an unwitnessed bowel movement, a photo will be taken at the time the bowel movement is observed, and entered into the EDC as an unwitnessed bowel movement. If multiple bowel movements are noted within a 15-minute time period, they can be considered as one bowel movement and the consistency will be determined based upon the highest PFS score observed and described.

A daily phone call will be attempted by the study staff to the owner/designee to confirm that the data entered into the EDC by the owner is correct. Every effort will be made by the site staff to speak to the owner/designee at least once within each 24 hour interval. If the site is unsuccessful, the site will note this in the EDC; however, this inability to make telephone contact will not be considered a protocol deviation.

Upon speaking with the owner/designee, any observations noted by the owner/designee will be assessed by the Investigator as a possible Adverse Event. Additionally, any new medications given to the dog by the owner will be entered into the Prior and Concomitant Medication page.

Observation Period

During the Observation Period (T>72 hr-T96 hr), the owner will continue to photograph their dog's bowel movements but no further dosing of test articles will be done. A daily phone call will be attempted by the study staff to the owner/designee to confirm that the data entered into the EDC by the owner is correct. Any observations noted by the owner/designee will be assessed by the Investigator as a possible Adverse Event. Additionally, any new medications given to the dog by the owner will be entered into the Prior and Concomitant Medication page. The Observation Period will be used to evaluate persistence of effect or recurrence of diarrheal signs upon withdrawal of IVP.

Final Evaluation (End of Study Procedures)

A dog will be considered to have completed the study upon successful completion of this visit and its procedures. A final physical exam will be conducted at the end of the Observation Period, or within 3 business days of the end of the Observation Period or at discontinuation (if a dog is discontinued, the site staff will attempt to have the owner bring the dog in to complete this visit. If this is not possible, the dog will be considered lost to follow up). Samples will be collected for clinical chemistry, hematology and urinalysis (urinalysis will be repeated only if the initial sample had clinically significant abnormalities). A final VCOG-CTCAE v1.1 Grade for diarrhea will also be assessed at the same time. The Investigator or co-Investigator will meet with the dog owner to review and confirm for accuracy the data in the daily diary, and ask about recrudescence of diarrheal signs with emphasis on the color and the frequency of any bowel movements following the completion of IP dosing.

The study may be terminated (i.e. not completed) at any time at the discretion of the Sponsor. The reason for termination will be documented in the study records.

Study Discontinuation

A dog may be discontinued from the study by its owner or by the Investigator for any reason and at any time.

In the event a dog discontinues the study, the same procedures should be conducted that are done at the Final Evaluation. If the reason for discontinuation is due to an AE, this will be documented on the AE form.

Adverse Events

Any clinically significant changes from the baseline (before treatment with IPs) in the dog's signs, behavior and fecal attributes will be reported by the dog's owner. Any clinically significant changes from the baseline in the dog's physical exam or laboratory values will be noted by the Investigator on the Adverse Event (AE) Form, as appropriate. The assessment of adverse events will also be ascertained via the daily phone calls between the dog owner and the Investigator or trained designee. Adverse events will be graded according to the ABON System.

Number of Animals

The enrollment target is at least 25 evaluable cases across all sites on IVP for the primary evaluation of efficacy. At least 12 additional evaluable cases on CP will be enrolled to allow for comparison of efficacy results between IVP and CP. The ratio of IVP to CP-treated dogs will be approximately 2:1. The Study will use at least three geographically diverse sites across the contiguous United States. The maximum enrollment for any given site is 40% of the total number of evaluable cases in the study.

As this is a pilot study, the sample size estimation is not based on statistical considerations. An evaluable sample size of at least 25 evaluable cases on IVP and 12 evaluable cases on CP is considered sufficient for the purposes of this study.

Blocking Factors

No blocking factors will be utilized in this study.

Randomization Procedures

A separate randomization list will be created for each study site by the Study Statistician. The Statistician will randomly allocate study treatments at a ratio of approximately 2:1 IVP:CP.

Blinding Procedures

This is a randomized, double-blinded study, therefore the Sponsor, the owner, the Investigator and all site study staff will be blinded to treatment. Owners will additionally be blinded to the previous recordings of their dog's bowel movements in the online data capture system so as not to influence their subsequent recording of bowel movements.

Investigational Products (IP)

Investigational Veterinary Product (IVP)

Proprietary Name: Crofelemer (CAS Number: 148465-45-6)

The IVP formulation will be manufactured according to the principles of GMP. A certificate of analysis for each formulation will be included in the final study report. The manufacturing site name and address, percent composition, lot/batch number, and expiry/retest date will be documented.

In addition to the active pharmaceutical ingredient (API) of crofelemer, the inactive ingredients include microcrystalline cellulose, croscarmellose sodium, colloidal silicon dioxide and magnesium stearate. The enteric-coating ingredients include ethylacrylate and methylacrylate copolymer dispersion, talc, triethyl citrate, xanthan gum, titanium oxide, propyl paraben and methyl paraben.

Dosage Form

The IVP will be supplied as unscored enteric-coated white tablets containing 125 mg of crofelemer.

Control Product (CP)

The CP will be manufactured according to the principles of GMP. A certificate of analysis will be included in the final study report. The manufacturing site name and address, percent composition, lot/batch number, and expiry/retest date will be documented.

The formulation of the CP will match that of the IVP but will not contain the active pharmaceutical ingredient (API).

Dosage Form

The CP will be supplied as unscored enteric-coated white tablets of the same size as the IVP containing 0 mg crofelemer.

Dose Justification

The dose for this study was based on data obtained from a pilot study that assessed the clinical effectiveness of crofelemer (SP-303) in alleviating clinical signs associated with secretory diarrhea in dogs (CANA-001) and the wide margin of safety established in 30-day (WIL-288006) and 9-month (WIL-288022) toxicity studies. Chronic safety of crofelemer in dogs was studied in a 9-month study during which tablets were administered in capsules once daily, 7 days per week, for 273 or 274 days to three groups of beagle dogs. Dosage levels were 50, 175 and 600 mg/kg/day, plus a concurrent control group. Based on the results of this study, the no-observed-adverse-effect level (NOAEL) for oral (capsule) administration of enteric-coated crofelemer tablets to dogs for 273 or 274 consecutive days was 50 mg/kg/day. At this dose level, findings were restricted to infrequent gastrointestinal signs. The results at the higher dosages (175 and 600 mg/kg/day) suggested that the primary adverse effect was gastrointestinal irritation, which in turn caused a variety of secondary effects (decreased body weight and food consumption, diarrhea, emesis, changes in hematology and serum chemistry parameters, decreased thyroid/parathyroid weights and/or macrophage infiltration with the presence of basophilic bodies and the uptake of pigment in the lymph nodes, gastrointestinal tract and liver). Thus, the no effect level is estimated to be between 50 and 175 mg/kg/day.

Safety Precautions for Study Personnel

Standard precautions for the safety of study personnel will be followed during the study. There are no special precautions for the dog owner to be aware of when administering the IPs. A safety data sheet (SDS) will be provided to the Site with each shipment of IPs.

Investigational Products Administration

A study initiation meeting will be held for each participating study site (either in-person or by webinar) to ensure that the Investigator and associated study personnel have a thorough understanding of the procedures and can explain such procedures to the dog owner regarding administration of IPs and collection of data.

At the time of study enrollment for each dog, the dog will be weighed and the Investigator will determine the dose from the following table:

TABLE 2

Dosage based on body weight

| Body Weight | Dose |
|---|---|
| 5 to 137 lb. (2.3 to 62 kg) | 1 tablet BID |

The first dose of the study treatment will be administered orally to the dog by the study staff while the dog is still at the study site. Dogs will then be dosed at home orally twice daily (12±2 hours apart) by their owner or designee for the remainder of the study. The dog owner will record the time of dose administration during the study. A vehicle such as a Greenies Pill Pocket™ may be used or a small ball of food, but is not required. After the dose has been administered, the dog will be observed briefly to ensure the tablet(s) have been swallowed and not spit out.

If a dog vomits within one hour after dosing, this observation will be recorded by the owner and the dog should be re-dosed with the same number of new tablets. If a dog vomits more than one hour after dosing, this observation should be recorded by the owner, but the dog should not be re-dosed at that time and will be considered dosed for that time point. If a dog vomits more than once after dosing, the dog should be discontinued from the study. The Investigator or designee will record each vomiting episode on the Adverse Event CRF.

TABLE 3

Test Animals And Case Identification

| CATEGORY | DESCRIPTION |
|---|---|
| Species | *Canis familiaris* (domestic dog) |
| Source | Client-owned animals |
| Breed | Any |
| Body Weight | 5 to 137 lb. (2.3 to 62 kg) |

TABLE 3-continued

Test Animals And Case Identification

| CATEGORY | DESCRIPTION |
|---|---|
| Age | ≥1 year of age |
| Gender | Male or female |
| Reproductive Status | Intact, spayed or neutered. No pregnant of lactating females |

A unique case number will be assigned to each dog enrolled in the study but no case number will be assigned to dogs whose owners sign an ICF but whose dogs are not formally screened and enrolled. At each site, case numbers will consist of a two-digit site identification number followed by a three-digit dog identification number. IPs will be dispensed to the owners based on the sequential numbering of each enrolled dog.

Effectiveness Variables

Primary Endpoint

Resolution of Diarrhea

Treatment success (resolution of diarrhea) will be defined as any dog that develops formed stool (PFS of 1, 2, 3, 4 or 5) and maintains formed stool (i.e.—no PFS of 6 or 7) or has no stool, for at least 24 hours during the Treatment Period (T0 hr-T72 hr). Therefore, resolution of diarrhea must occur by T48 hr.

A treatment failure will be defined as any dog that does not achieve a formed stool (PFS of 1, 2, 3, 4 or 5) for at least 24 hours during the Treatment Period (T0 hr-T72 hr), and/or any of the following is experienced:

1. Withdrawal of Owner Consent due to perceived lack of efficacy

2. Adverse event that prevents its continued participation in the study

Secondary Endpoints

Resolution of Diarrhea Over the Entire Treatment Period

Treatment success (resolution of diarrhea) will be defined as any dog that develops formed stool (PFS of 1, 2, 3, 4 or 5) and maintains formed stool (i.e.—no PFS of 6 or 7) or has no stool, during the Treatment Period (T0 hr-T72 hr).

A treatment failure will be defined as any dog that does not achieve a formed stool (PFS of 1, 2, 3, 4 or 5) during the Treatment Period (T0 hr-T72 hr), and/or any of the following is experienced:

1. Withdrawal of Owner Consent due to perceived lack of efficacy

2. Adverse event that prevents its continued participation in the study 12.2.2 Comparison of Diarrhea VCOG-CTCAE v1.1 Grade at Screening and at Final Evaluation The VCOG-CTCAE v1.1 Grade for diarrhea taken at Screening for each dog will be compared to the VCOG-CTCAE v1.1 Grade for diarrhea taken at T72 h, T96 h and at Final Evaluation. The change in Grade between Screening and T72 h, T96 h and the Final Evaluation will be compared between the dogs that received IVP and the dogs that were given CP.

Time to Last Unformed Stool

Time to the last unformed stool (TLUS) will be determined by the elapsed time between the first dose (T0 hr) and the last unformed stool (PFS of 6 or 7) during the 72-hour Treatment Period only (T0 hr-T72 hr).

Frequency of Loose or Watery Diarrhea

The frequency of loose or watery diarrhea (PFS of 6 or 7) will be determined by the total number of unformed stool episodes (PFS of 6 or 7) occurring during the Study Period: T0 hr-T96 hr. (To be analyzed in 24-hour periods.)

Safety

Safety assessments will be made on the basis of signs reported by the owner as well as physical exam findings made by the Investigator and any abnormalities in laboratory work throughout the study.

Fecal Assessment

Purina Fecal Score (PFS)

Using the Purina Fecal Scoring (PFS) Chart, a PFS will be obtained at screening via communication with the dog owner and ideally with one or more photos of the dog's bowel movements. Each daily evaluation of PFS will be described by the dog owner and reviewed by telephone between the dog owner and the Investigator or trained designee.

Each fecal assessment will only consider new bowel movements produced since the previous fecal assessment. If the dog has experienced two or more bowel movements during a 15-minute period, then these bowel movements will be collectively noted and a single PFS assigned, with the highest PFS numerical score appropriate for the bowel movements recorded on the CRF.

Number of Bowel Movements

Throughout each day during the Study Period, the dog owner/designee will record each episode of bowel movements with a photo uploaded onto the eCRF. If the dog has experienced two or more bowel movements during a 15-minute period, then these bowel movements will be collectively noted as one event. After each episode of bowel movements and recording of the time and photo, the next episode of bowel movement(s) will be considered a separate event.

Statistical Analysis

All statistical tests will be 2-sided. Effectiveness will be evaluated at a 5% significant level. All tests will be performed using SAS version 9.3 or higher.

Statistical Analysis Populations

As this is a proof-of-concept study, the effectiveness analyses will include all dogs that were randomized and received at least one dose of the study medication (safety population/Intent-to-Treat (ITT) population).

Effectiveness

Primary Effectiveness Variable: Resolution of Diarrhea

The primary effectiveness variable 'resolution of diarrhea' will be dichotomized (success vs failure) and the proportion of success between the treatment groups during the treatment period (T0 hr-72 hr) will be compared. Possible differences between treatment groups will be assessed by a generalized linear mixed model (using SAS® Proc GLIMMIX assuming a binomial distribution and logit link). The model will include the fixed effect of Treatment (IVP or CP), Site and Treatment by Site interaction as random effects with baseline PFS as a covariate.

Treatment effectiveness will be concluded if there is a significant difference in the success rates between the two treatment groups and percent success is higher in the IVP group compared with the CP group.

Secondary Effectiveness Variables

Resolution of Diarrhea Over the Entire Treatment Period

The effectiveness variable 'resolution of diarrhea over the entire Treatment Period' will be dichotomized (success vs failure) and the proportion of success between the treatment groups during the treatment period (T0 hr-72 hr) will be compared. Possible differences between treatment groups will be assessed by a generalized linear mixed model (using SAS® Proc GLIMMIX assuming a binomial distribution and logit link). The model will include the fixed effect of Treatment (WP or CP), Site and Treatment by Site interaction as random effects with baseline PFS as a covariate.

Treatment effectiveness will be concluded if there is a significant difference in the success rates between the two treatment groups and percent success is higher in the IVP group compared with the CP group.

Comparison of Diarrhea VCOG-CTCAE v1.1 Grade at Screening and at Final Evaluation The change in Grade between Screening and the Final Evaluation will be compared between the dogs that received IVP and the dogs that were given CP using analysis of covariance (ANCOVA) modeling with treatment as a fixed effect, and site and treatment by site interaction as random effects with baseline PFS as a covariate.

Time to Last Unformed Stool

Time to last unformed stool (TLUS) will be presented using Kaplan-Meier methods and compared using a log-rank test. Dogs without a formed stool (score of 6 or 7) will be censored at the time of the last unformed stool. For dogs with only formed stool (scores of 1, 2, 3, 4 or 5) or no stool, the time of occurrence for TLUS will be set to zero.

Frequency of Diarrhea

ANCOVA modeling with treatment as a fixed effect, and site and treatment by site interaction as random effects with baseline PFS as a covariate will be employed to compare the frequency of diarrhea between IVP and CP.

Example 2: A Study of Diarrhea Prevention and Prophylaxis with Crofelemer in HER2 Positive Breast Cancer Patients (Human Subjects)

Study Design: Chemotherapy induced diarrhea is seen in up to 40-80% of patients receiving this treatment for HER2 positive locally advanced or metastatic breast cancer. This diarrhea can significantly impact a patient's quality of life and ability to tolerate chemo/anti-HER2 therapy. This study will look at the efficacy of the drug crofelemer in preventing diarrhea in breast cancer patients receiving trastuzumab, pertuzumab, and docetaxel or paclitaxel with or without carboplatin (chemotherapeutic regimens referred to as THP and TCHP).

Protocol:

Approximately 46 patients will be randomly assigned to the treatment arm or the control. Patients on the treatment arm will take one tablet of crofelemer twice a day (each tablet is 125 mg), to be swallowed whole without chewing or crushing, during cycles 1-2 of chemotherapy with THP or TCHP. Patient will be monitored off crofelemer during cycle 3 of chemotherapy. Patients on the control arm will be on the study for cycles 1-3 of THP or TCHP. Patients on the control arm will not receive crofelemer at any time on this study. A cycle can comprise an infusion of the prescribed THP or TCHP followed by a 21 day duration. See Baselga J, Cortés J, Kim S B, et al. Pertuzumab plus Trastuzumab plus Docetaxel for Metastatic Breast Cancer. N Engl J Med. 2012; 366:109-119).

Eligibility Criteria:

Patients eligible for the study much be as follows: Willing and able to provide written informed consent; man or woman ≥18 years of age; pathologically confirmed diagnosis of HER2 positive breast cancer of any stage (previous treatment is allowed without limits on lines of prior therapy); scheduled to receive at least 3 consecutive cycles of THP or TCHP; have a performance status of 0-2 according to the ECOG scale; have a negative pregnancy test at time of informed consent for women of childbearing potential; have a Left Ventricular Ejection Fraction (LVEF) greater or equal to 50% at baseline as determined by either ECHO or MUGA; and be able to read, understand, follow the study procedure and complete crofelemer, rescue medication, and bowel movement diaries. Patients with brain metastases (including concurrent steroid treatment) are allowed on this study. Patients not eligible for the study include women who are breastfeeding; those with ongoing irritable bowel syndrome (IBS) or colitis (including but not limited to ulcerative colitis, Crohn's disease, microscopic colitis, etc.); those using investigational drugs within 3 weeks of signing consent or foreseen use during the study, chemotherapy, trastuzumab, or pertuzumab within the past 3 weeks, laxatives within the past 7 days, chronic laxatives (≥30 consecutive days), or anti-diarrheal agents (including but not limited to loperamide, octreotide, bismuth, tincture of opium, atropine, probiotics in any form other than food) within the past 7 days, antibiotics within the past 7 days. Patients are also excluded if they have any of the following: any type of ostomy; total colectomy; fecal incontinence; ongoing radiation induced diarrhea or constipation or planned radiotherapy to the abdomen or pelvis while on study; active systemic infection requiring ongoing intervention, including but not limited to oral and intravenous antibiotics, anti-fungals, anti-parasites, anti-virals; major abdominal or pelvic surgery within the past 6 months; inadequate organ function for starting THP or TCHP, which may include the following laboratory results within 28 days prior to signing consent: total bilirubin>upper limit of normal (ULN) (unless the patient has documented Gilbert's syndrome); serum creatinin>2.0 mg/dL or 177 µmol/L; or AST (SGOT) and ALT (SPGT)>2.5 ULN.

Effectiveness Variables:

Primary outcome measures All-grade diarrhea [Time Frame: 29 months]: Incidence of all grade diarrhea lasting 2 or more consecutive days during cycles 1 and 2 of chemotherapy Secondary outcome measures as follows:

Diarrhea any grade [Time Frame: 29 months] Incidence of diarrhea of any grade, as measured by CTCAE v4.0, by cycle and by stratum Grade 3-4 diarrhea [Time Frame: 29 months] Incidence of diarrhea of grade 3-4, as measured by CTCAE v4.0, by cycle and by stratum Diarrhea onset [Time Frame: 29 months] Time to onset of first episode of diarrhea of any grade, overall and by stratum Diarrhea duration [Time Frame: 29 months] Duration (days) of any grade diarrhea, defined from day 1 to day 21, by cycle in which the episode started and by stratum Duration grade 3-4 diarrhea [Time Frame: 29 months] Duration (days) of grade 3-4 diarrhea, defined from day 1 to day 21, by cycle in which the episode started and by stratum Anti-diarrheal medications [Time Frame: 29 months] Use of anti-diarrheal medications (other than study drug), by cycle and grade FACIT-D total score [Time Frame: 29 months] Quantitative FACIT-D total score, collected day 1 of each cycle and at the time of study completion, by cycle and by stratum FACIT-D diarrhea score [Time Frame: 29 months] Quantitative FACIT-D diarrhea subset (DS) score, by cycle and by stratum Stool frequency and consistency [Time Frame: 29 months] Frequency table of stool consistency, as measured by the Bristol Stool scale, by cycle stratum between treatment groups All publications, patents, and patent applications cited herein are hereby incorporated herein by reference in their entirety.

What is claimed is:

1. A method of treating chemotherapy-induced diarrhea (CID) in a human subject undergoing chemotherapy comprising administering to a subject in need thereof a composition comprising an effective amount of crofelemer to treat CID, wherein the chemotherapeutic is neratinib.

2. The method of claim 1, wherein the crofelemer may be administered in combination with other chemotherapy agents.

3. The method of claim 1, wherein the crofelemer is administered at the same time as chemotherapy to reduce or delay the onset of CID.

4. The method of claim 1, wherein the crofelemer is administered before chemotherapy to prevent, reduce or delay the onset of CID.

5. The method of claim 1, wherein the crofelemer is administered after chemotherapy to reduce the onset of or treat CID.

6. The method of claim 1, wherein the crofelemer is administered after a subject begins to exhibit symptoms of CID.

7. The method of claim 1, wherein the crofelemer is administered for the duration of treatment with the chemotherapy.

8. The method of claim 1, wherein the crofelemer is administered until symptoms of CID are ameliorated and then crofelemer is discontinued.

9. The method of claim 1, wherein the administering comprises administering about 250 mg to about 1000 mg per day; administering about 250 mg per day; administering about 500 mg per day; administering about 1000 mg per day; administering about 125 mg two times per day; administering about 250 mg two times per day; or administering about 500 mg two times per day of crofelemer to a subject in need thereof.

10. The method of claim 1, wherein the crofelemer is administered as an enteric coated oral dosage form.

11. The method of claim 1, wherein the crofelemer is administered as an oral dosage form that is not enteric coated.

12. The method of claim 1, wherein the subject can tolerate a chemotherapeutic agent that the subject could not tolerate without the administration of crofelemer or can tolerate a higher dosage of chemotherapeutic than the subject could tolerate without administration of crofelemer.

13. The method of claim 1, wherein a subject is considered treated if the subject demonstrates one or more of a decrease in the number of bowel movements per day, a decrease in the number of watery bowel movements per day, an improvement in the daily abdominal score for pain or discomfort, an improvement in the score for daily stool consistency, a decrease in stool consistency, a decrease in the number of days per week that subjects experienced urgency, a decrease in the number of days per week that subjects experienced fecal incontinence, or a decrease in the unscheduled visit for a significant worsening of diarrhea.

14. The method of claim 1, wherein the administration results in a decrease in 1, 2 or 3 Grades of the Grade of diarrhea according to the Common Toxicity Criteria.

15. The method of claim 1, wherein the subject is undergoing chemotherapy to treat a cancer selected from breast cancer, ovarian cancer, prostate cancer, bladder cancer, cervical cancer, uterine cancer, testicular cancer, kidney cancer, thyroid cancer, oral or oropharyngeal cancer, astrocytoma, sarcoma, mesothelioma, meningioma, lymphoma, myeloma, head and neck cancer, lung cancer, carcinoma, malignant melanoma, peritoneal cancer, gastric cancer, hepatic cancer, colorectal cancer, gallbladder cancer, bone cancer, pancreatic cancer, tongue cancer, esophageal cancer, brain tumor, brain stem glioma, a metastases thereof, and leukemia.

16. A method of treating CID in a human subject undergoing chemotherapy for HER positive breast cancer, said method comprising administering to said human subject a composition comprising crofelemer at a dose of 125 mg twice per day, wherein the chemotherapy is neratinib with or without carboplatin.

* * * * *